(12) United States Patent
Gershenson

(10) Patent No.: US 10,089,734 B1
(45) Date of Patent: Oct. 2, 2018

(54) EQUIVALENT WAVE FIELD PROCESSING OF THERMAL IMAGES

(71) Applicant: Meir Gershenson, Cholul Yucatan (MX)

(72) Inventor: Meir Gershenson, Cholul Yucatan (MX)

( * ) Notice: Subject to any disclaimer, the term of this patent is extended or adjusted under 35 U.S.C. 154(b) by 0 days.

(21) Appl. No.: 15/876,200

(22) Filed: Jan. 21, 2018

(51) Int. Cl.
*G06T 7/00* (2017.01)
*H04N 5/33* (2006.01)
*H04N 5/225* (2006.01)
*G01N 27/72* (2006.01)
*G01J 5/00* (2006.01)
*G01N 25/72* (2006.01)

(52) U.S. Cl.
CPC .......... *G06T 7/0004* (2013.01); *G01J 5/0003* (2013.01); *G01N 25/72* (2013.01); *H04N 5/2256* (2013.01); *H04N 5/33* (2013.01); *G01J 2005/0077* (2013.01); *G06T 2207/10048* (2013.01); *G06T 2207/20048* (2013.01); *G06T 2207/30164* (2013.01)

(58) Field of Classification Search
CPC .... A61B 8/5207; G06K 9/629; G06T 7/0004; H04N 5/33; H04N 5/2256; G01N 25/72
See application file for complete search history.

(56) References Cited

U.S. PATENT DOCUMENTS

| | | | |
|---|---|---|---|
| 6,147,636 A | 11/2000 | Gershenson | |
| 7,724,925 B2 | 5/2010 | Shepard | |
| 8,947,659 B1* | 2/2015 | Baastians | H01L 31/107 356/301 |
| 2004/0004569 A1* | 1/2004 | Lam | G01S 13/9035 342/351 |
| 2005/0008215 A1* | 1/2005 | Shepard | G01N 25/72 382/141 |
| 2005/0069207 A1* | 3/2005 | Zakrzewski | B64D 45/0015 382/190 |

OTHER PUBLICATIONS

Burgholzer, Peter, et al. "Three-dimensional thermographic imaging using a virtual wave concept." *Journal of Applied Physics* 121.10 (2017): 105102.

(Continued)

*Primary Examiner* — Kenny Cese
(74) *Attorney, Agent, or Firm* — Pearl Cohen Zedek Latzer Baratz LLP

(57) ABSTRACT

A system for thermal transient imaging of an object includes a radiation source configured to irradiate the object with radiation in accordance with an excitation profile. An imaging device includes an array of detector pixels and is configured to detect thermal radiation from a surface of the object. A processor is configured to obtain a series of frames of thermal image data of the surface acquired by the imaging device over time when the object is irradiated by the radiation source. The processor is further configured to process, using the excitation profile, the series of frames of thermal image data to transform the thermal image data to an equivalent wave field representation that represents a series of depth-resolved virtual images of the object.

16 Claims, 2 Drawing Sheets

(56) References Cited

OTHER PUBLICATIONS

Gershenson, Meir. "Synthetic aperture processing of electromagnetic sounding in conductive media." *Subsurface Sensors and Applications*. vol. 3752. International Society for Optics and Photonics, 1999.
Gershenson, Meir. "Analysis of pulse thermography using similarities between wave and diffusion propagation." *Thermosense: Thermal Infrared Applications XXXIX*. vol. 10214. International Society for Optics and Photonics, 2017.
Gershenson, Meir . "Simple interpretation of time-domain electromagnetic sounding using similarities between wave and diffusion propagation." *Geophysics* 62.3 (1997): 763-774.

\* cited by examiner

US 10,089,734 B1

EQUIVALENT WAVE FIELD PROCESSING OF THERMAL IMAGES

FIELD OF THE INVENTION

The present invention relates to nondestructive testing. More particularly, the present invention relates to equivalent wave field processing of thermal images.

BACKGROUND OF THE INVENTION

Transient thermal imaging or flash thermography uses a pulsed heat source, such as xenon flash lamp or conventional incandescent light bulb, to heat the surface of an object. The duration of each pulse may range from few milliseconds for a flash lamp source to a few seconds for incandescent lamp source. An infrared video camera monitors the temperature of the surface on one of the sides of the object, typically the same side that is irradiated by the heat source. Analysis of the monitored temperature may yield information regarding internal features of the object. For example, the analysis may be used to detect and locate flaws, voids, or damage to the internal structure of the object.

SUMMARY OF THE INVENTION

There is thus provided, in accordance with an embodiment of the present invention, a system for thermal transient imaging of an object, the system including: a radiation source configured to irradiate the object with radiation in accordance with an excitation profile; an imaging device including an array of detector pixels and configured to detect thermal radiation from a surface of the object; and a processor configured to: obtain a series of frames of thermal image data of the surface acquired by the imaging device over time when the object is irradiated by the radiation source; and process, using the excitation profile, the series of frames of thermal image data to transform the thermal image data to an equivalent wave field representation that represents a series of depth-resolved virtual images of the object.

Furthermore, in accordance with an embodiment of the present invention, the system includes a data storage that is configured to store one or a plurality of transformations that are applicable to the thermal image data to transform the thermal image data to the equivalent wave representation.

Furthermore, in accordance with an embodiment of the present invention, a transformation of the one or a plurality of transformations is a linear transformation.

Furthermore, in accordance with an embodiment of the present invention, the transformation of the one or a plurality of transformations, and that is applicable to a pixel of the time series of the frames that are acquired at times $t_d$, is representable by an inverse of a matrix of the form $$W(t_d, t_w) = \mathcal{L}^{-1}\left\{e^{-\sqrt{s}t_w}\frac{H_d(s)}{H_w(\sqrt{s})}, t_d\right\},$$

where $t_w$ represents a virtual time of each of the virtual images, $\mathcal{L}^{-1}$ represents the inverse Laplace transform, $H_d(s)$ represents a Laplace transform of thermal excitation by the radiation source, $H_w(\sqrt{s})$ represents the Laplace transform of a virtual wave excitation, and s is a Laplace transform variable.

Furthermore, in accordance with an embodiment of the present invention, the virtual wave excitation is a Dirac delta function of $t_w$ or a derivative of the Dirac delta function of $t_w$.

Furthermore, in accordance with an embodiment of the present invention, the virtual wave excitation is selected to be a Dirac delta function of $t_w$ when the radiation source is configured to irradiate the object with spot illumination, and to be the derivative of the Dirac delta function of $t_w$ when the radiation source is configured to irradiate the object with flood illumination.

Furthermore, in accordance with an embodiment of the present invention, the thermal excitation is a Dirac delta function of $t_d$ or a step function of $t_d$.

Furthermore, in accordance with an embodiment of the present invention, wherein the transformation of the one or a plurality of transformations is representable as the inverse of the matrix W with an excitation profile of the radiation source.

Furthermore, in accordance with an embodiment of the present invention, the processor is further configured to perform principal component analysis of the thermal image data to obtain the excitation profile.

Furthermore, in accordance with an embodiment of the present invention, the processor is further configured to apply synthetic aperture processing to the thermal image data.

Furthermore, in accordance with an embodiment of the present invention, the processor is further configured to apply principal component analysis to the equivalent wave field representation.

There is further provided, in accordance with an embodiment of the present invention, a method for thermal transient imaging of an object, the method including: obtaining a series of frames of thermal image data of a surface of the object that were acquired by an imaging device over time when the object is irradiated with radiation by a radiation source in accordance with a radiation profile; obtaining a transformation that corresponds to the radiation profile; and applying the transformation to the time series of frames to transform the thermal image data to an equivalent wave field representation that represents a series of depth-resolved virtual images of the object.

Furthermore, in accordance with an embodiment of the present invention, obtaining the transformation that is applicable to a pixel of the time series of the frames that are acquired at times $t_d$ includes calculating an inverse of a matrix of the form $$W(t_d, t_w) = \mathcal{L}^{-1}\left\{e^{-\sqrt{s}t_w}\frac{H_d(s)}{H_w(\sqrt{s})}, t_d\right\},$$

where $t_w$ represents a virtual time of each of the virtual images, $\mathcal{L}^{-1}$ represents the inverse Laplace transform, $H_d(s)$ represents a Laplace transform of thermal excitation by the radiation source, $H_w(\sqrt{s})$ represents the Laplace transform of a virtual wave excitation, and s is a Laplace transform variable.

Furthermore, in accordance with an embodiment of the present invention, calculating the inverse includes applying singular value decomposition or Tikhonov regularization to the matrix W.

Furthermore, in accordance with an embodiment of the present invention, obtaining the transformation includes selecting the virtual wave excitation to be a Dirac delta function of $t_w$ when the object is irradiated with spot illumination, and to be the derivative of the Dirac delta function of $t_w$ when the object is irradiated with flood illumination.

Furthermore, in accordance with an embodiment of the present invention, the thermal excitation is a Dirac delta function of $t_d$ or a step function of $t_d$.

Furthermore, in accordance with an embodiment of the present invention, obtaining the transformation further includes convolving the matrix W with an excitation profile of the radiation source prior to inverting the matrix.

Furthermore, in accordance with an embodiment of the present invention, obtaining the transformation further includes performing principal component analysis of the thermal image data to obtain the excitation profile.

Furthermore, in accordance with an embodiment of the present invention, the method includes applying synthetic aperture processing to the thermal image data.

Furthermore, in accordance with an embodiment of the present invention, the method includes applying principal component analysis to the equivalent wave field representation.

BRIEF DESCRIPTION OF THE DRAWINGS

In order for the present invention to be better understood and for its practical applications to be appreciated, the following Figures are provided and referenced hereafter. It should be noted that the Figures are given as examples only and in no way limit the scope of the invention. Like components are denoted by like reference numerals.

DETAILED DESCRIPTION OF THE INVENTION

Figure 1:
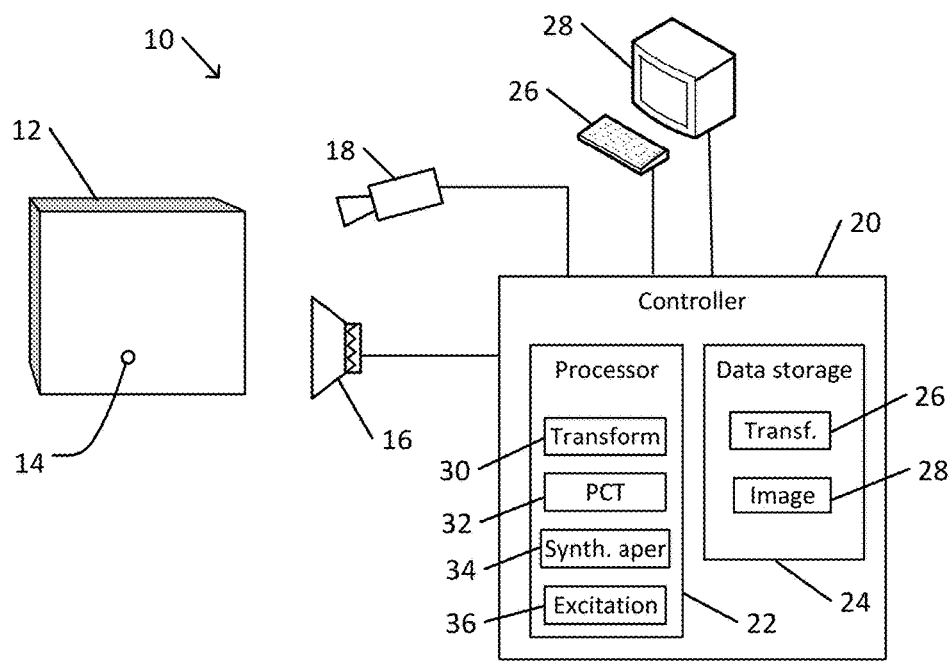
FIG. 1 schematically illustrates a system for equivalent wave field processing of thermal transient infrared images, in accordance with an embodiment of the present invention.

In the following detailed description, numerous specific details are set forth in order to provide a thorough understanding of the invention. However, it will be understood by those of ordinary skill in the art that the invention may be practiced without these specific details. In other instances, well-known methods, procedures, components, modules, units and/or circuits have not been described in detail so as not to obscure the invention.

Although embodiments of the invention are not limited in this regard, discussions utilizing terms such as, for example, "processing," "computing," "calculating," "determining," "establishing", "analyzing", "checking", or the like, may refer to operation(s) and/or process(es) of a computer, a computing platform, a computing system, or other electronic computing device, that manipulates and/or transforms data represented as physical (e.g., electronic) quantities within the computer's registers and/or memories into other data similarly represented as physical quantities within the computer's registers and/or memories or other information non-transitory storage medium (e.g., a memory) that may store instructions to perform operations and/or processes. Although embodiments of the invention are not limited in this regard, the terms "plurality" and "a plurality" as used herein may include, for example, "multiple" or "two or more". The terms "plurality" or "a plurality" may be used throughout the specification to describe two or more components, devices, elements, units, parameters, or the like. Unless explicitly stated, the method embodiments described herein are not constrained to a particular order or sequence. Additionally, some of the described method embodiments or elements thereof can occur or be performed simultaneously, at the same point in time, or concurrently. Unless otherwise indicated, the conjunction "or" as used herein is to be understood as inclusive (any or all of the stated options).

Some embodiments of the invention may include an article such as a computer or processor readable medium, or a computer or processor non-transitory storage medium, such as for example a memory, a disk drive, or a USB flash memory, encoding, including or storing instructions, e.g., computer-executable instructions, which when executed by a processor or controller, carry out methods disclosed herein.

In accordance with an embodiment of the present invention, transient thermal imaging includes processing acquired thermal images to generate an equivalent wave field. In transient thermal imaging, an object is externally irradiated with pulsed radiation or other time varying radiation (e.g., step radiation where the radiation source is turned on and remains on during the measurement, or where the radiation is emitted until the measurement begins). When the object is being irradiated (e.g., concurrently with the irradiation or after the irradiation), a thermal imaging device (e.g., a thermal infrared camera or other device configured to yield a map of instantaneous temperature of a surface) may acquire a time series of thermal image data of a surface of the object. The thermal image data may be indicative of a temperature of one or more points or regions of the surface as a function of time. In some cases, the thermal imaging device may include a single thermal detector (e.g., that may be scanned across the device).

The time series of thermal image data may be processed to convert the thermal image data to an equivalent wave field data. Since the equivalent wave field data may be characterized by a wave equation and wave velocity, the equivalent wave field data may be processed to yield a series of depth-resolved images, each representing a flat or curved slice of the object at a particular depth into the object or distance from a point on the surface of the object. In each depth-resolved image, a point or region whose value (e.g., indicative of temperature) differs significantly from its surroundings may be indicative of a flaw or other feature of the object at the depth and lateral position corresponding to that point or region.

As used herein, pulsed radiation refers to any radiation whose intensity varies over time, regardless of duration of each radiation pulse or of an interval between successive pulses, of a shape of the pulse (e.g., sharp or gradual increase or decline in intensity at the beginning and end, respectively, of each pulse), or of a value of the intensity of the radiation between pulses (e.g., whether negligible, or having an appreciable value between pulses).

For example, the thermal image data may be represented by a thermal data function $x_d(r, t)$, where r represents position and t represents time, the value of thermal data function $x_d$ being indicative of temperature. Typically, thermal data function $x_d(r,t)$ may satisfy a diffusion equation of the form:

$$\nabla^2 x_d(r, t) - k/(\rho C) \cdot \frac{\partial}{\partial t} x_d(r, t) = g_d(r, t),$$

where k represents thermal conductivity, ρ represents mass density, C represents specific heat, and $g_d(r,t)$ represents thermal excitation by the radiation source.

The equivalent wave field may be represented by an equivalent wave function $x_w(r, t)$ having a value representing a wave amplitude, and satisfying a wave equation of the form $$\nabla^2 x_w(r, t) - v^{-2} \cdot \frac{\partial^2}{\partial t^2} x_w(r, t) = g_w(r, t),$$

where v represents the wave velocity and $g_w(r,t)$ represents a virtual wave excitation.

The equivalent wave function may be calculated from the thermal data function, e.g., by representing the relationship between the two functions in the form of a matrix equation. For example, the thermal data vector $X_d$ may represent a value (e.g., temperature or radiance) of a single pixel of the thermal image over time $t_d$. For example, time $t_d$ may correspond to the time when each thermal image is acquired, e.g., starting from the time of excitation by a pulse of the radiation. Typically, successive times $t_d$ are at substantially equal time intervals. Alternatively or in addition, the thermal image data may be represented in another form.

Similarly, the equivalent wave vector $X_w$ may represent the equivalent wave field at the pixel location vector as a function of virtual time $t_w$. Alternatively or in addition, the equivalent wave data may be represented in another form.

A transformation that relates the thermal image data to the equivalent wave representation may be may be represented as a transformation matrix equation $X_d = W \cdot X_w$. The transformation matrix W may be expressed as $$W(t_d, t_w) = \mathcal{L}^{-1}\left\{e^{-\sqrt{s}t_w}\frac{H_d(s)}{H_w(\sqrt{s})}, t_d\right\},$$

where $\mathcal{L}$ represents the Laplace transform and $\mathcal{L}^{-1}$ represents the inverse Laplace transform, $H_d(s)$ represents the Laplace transform of the thermal excitation by the heat source, $\mathcal{L}\{h(t_d)\}$, $H_w(\sqrt{s})$ represents the Laplace transform of the virtual wave excitation, $\mathcal{L}\{h_w(t)\}$, and s is the Laplace transform variable. Alternatively or in addition, the transformation may be represented in another form.

For example, in some cases, it is advantageous to use a virtual wave excitation in the form of an instantaneous pulse in time, represented by the Dirac delta function $\delta(t_w)$. When the thermal excitation is also instantaneous, represented by a thermal excitation function in the form of $\delta(t_d)$, then $W(t_d, t_w)$ takes the form $$\frac{t_w}{\sqrt{4\pi t_d^3}}e^{-\left(\frac{t_d^2}{4t_d}\right)}.$$

When the thermal excitation represented by a thermal excitation function in the form of a step function $\Phi(t_d)$, then $W(t_d,t_w)$ takes the form $$\text{erfc}\left(\frac{t_w}{\sqrt{4t_d}}\right),$$

where erfc represents the complementary error function. When the thermal excitation is represented by a thermal excitation function in the form of an impulse of width $\Delta t_d$, then $W(t_d, t_w)$ may take the $$\text{erfc}\left(\frac{t_w}{\sqrt{4t_d}}\right) - F(t_w - \Delta t_d)\text{erfc}\left(\frac{t_w}{\sqrt{4(t_d - \Delta t_d)}}\right).$$

When the virtual wave excitation is the derivative of the Dirac delta function $d\delta(t_w)/dt_w$ and the thermal excitation is again represented by a thermal excitation function in the form of $\delta(t_d)$, then $W(t_d, t_w)$ may take the form $$\frac{1}{\sqrt{4\pi t_d}}e^{-\left(\frac{t_d^2}{4t_d}\right)}.$$

The virtual wave vector $X_w$ (e.g., indicative of temperature of a pixel of the image as a function of depth within the object) may be calculated by inverting the transformation matrix equation above, e.g., $X_w = W^{-1} X_d$.

In some cases, e.g., in the cases of a radiation source in the form of a xenon flash or similar source with negligible rise time and fall time, the actual irradiation as a function of time may closely correspond with one of the thermal excitation functions described above. In other cases, e.g., in the case of an incandescent lamp radiation source, the actual excitation profile (irradiation as a function of time) may differ greatly from the forms discussed above. However, direct calculation of the corresponding Laplace transforms may be computationally difficult.

In such a case, an initial transformation matrix may be calculated for $\delta(t_d)$ thermal excitations described above. The resulting $W(t_d,t_w)$ may then be convolved with an actual, e.g., measured, calculated, or modeled, excitation profile $h(t_d)$ of the radiation source to yield a modified transformation matrix $W'(t_d,t_w) = W(t_d,t_w) * h(t_d)$, where * represents the convolution operation $u(x) * v(x) = \int_0^x u(y) \cdot v(x-y) dy$. In this case, the virtual wave vector $X_w$ may be calculated by inverting the modified transformation matrix, e.g., $X_w = W'^{-1} \cdot X_d$.

In practice, since the determinant of W (or W') may be very small, straightforward inversion of W may not be practicable. Techniques that may be applied to invert W may include singular value decomposition (SVD), Tikhonov regularization, or other techniques known in the art.

The virtual wave vectors corresponding to different pixels of the thermal images may be assembled to form a series of virtual frames, each at a different virtual time $t_w$. In many cases (e.g., where the determinant of W is small), it may be possible to reduce the number of virtual frames without loss of information. For example, the number of frames may be reduced by a factor of between 3 and 30. In some cases, e.g., where the original thermal data is noisy, even larger reductions may be practical.

Since the transformation from $X_d$ to $X_w$ is linear, linear relationships between thermal image frames (e.g., data in a thermal image frame that is related by linear interpolation or extrapolation to data in earlier or later frames) will be present in the virtual frames. For example, principal component thermometry (PCT) may be applied to detect such relationships. Application of principal component thermometry may, for example, separate signals resulting from structure of the object from random effects of noise. Detected linear relationships may enable reducing the number of frames, e.g., where the pixel values in a sequence of frames are linearly related, e.g., by linear interpolation, to one another.

A typical principal component thermometry involves operations based on a single image data matrix that includes all of the image data. The dimensions of the image data matrix are the number of pixels in each image by the number of acquired image frames. For example, as SVD calculation may include creation of a square covariance matrix of dimension N may then be created by multiplying the image data matrix by its transpose. The number of computation operations in a typical SVD calculation may be proportional to $N^3$. Since, as discussed above, the number of virtual frames may be reduced, performing the PCT calculation on virtual frames may significantly reduce the number of computation operations. For example, reducing the number of virtual frames by a factor of 5 may reduce the number of computation operations by a factor of 125. The results of application of PCT to virtual frames may be transformed back to the form of thermal image data.

The PCT calculation may be applied in order to obtain a measured value of profile $h(t_d)$ of the radiation source. For example, a PCT calculation may be applied, e.g., as described above. The PCT analysis may yield the principal component (a zero component) that corresponds to the temperature response $T(t_d)$ of the surface of the object that is closest to a radiation source with an excitation profile $h(t_d)$.

For example, in the case of instantaneous flood illumination (uniform $\delta(t_d)$ irradiation of the surface), temperature response may be expected to be described by the equation $T(t_d)=a\, h(t_d)*t_d^{-1/2}$, where a represents a value dependent on material properties of the object, the geometry, and the radiation source, and * represents convolution. Similarly, in the case of spot illumination (irradiation of a limited region of the surface), $T(t_d)=a\, h(t_d)*t_d^{-3/2}$. Thus, excitation profile $h(t_d)$ may be determined from $T(t_d)$, up to a multiplicative factor. In the case that a mathematical model of the radiation source is available, e.g., such that the calculation of $W(t_d, t_w)$ is more accurate than one based on an arbitrarily selected thermal excitation function, the calculation of $h(t_d)$ may be increased accordingly.

Thus, a procedure for equivalent wave field processing of thermal image data of a surface of an object that is illuminated by a radiation source may include obtaining thermal image data, e.g., in the form of successive frames of thermal images. For example, thermal image data may be acquired or previously acquired and stored thermal image data may be retrieved. For purposes of the calculation, a time sequence of the thermal image data acquired by each pixel of the thermal image may be represented as a vector.

A transformation matrix W that is appropriate to the radiation source may be constructed or selected (e.g., from a set of stored transformation matrices W). For example, if the irradiation is flood illumination, transformation matrix W based on a virtual wave excitation in the form of the derivative of a Dirac delta function may provide a sharp response. For other illumination, the virtual wave excitation may take the form of a Dirac delta function.

When the radiation source is a flash source, the thermal excitation function may have the form of a Dirac delta function. If the profile of the radiation source is not well described by a Dirac delta function (e.g., an incandescent lamp with a relatively slow response time), an excitation profile may be obtained (e.g., may be calculated from processed data as described above, or may be obtained otherwise). Transformation matrix W may then be convolved with the excitation profile to yield a modified transformation matrix W'.

An inverse $W^{-1}$ of the transformation matrix or $W'^{-1}$ of the modified transformation matrix (or other representation of the inverse transformation from thermal image date to equivalent wave field data) may be obtained. For example, an appropriate inversion technique, such as SVD, Tikhonov regularization, or another appropriate technique, may be applied to W or to W' to obtain $W^{-1}$ or $W'^{-1}$, respectively. Alternatively or in addition, a previously calculated and stored inverse transformation matrix $W^{-1}$ or $W'^{-1}$ may be retrieved.

The inverse transformation, e.g., as represented by inverse transformation matrix $W^{-1}$ or otherwise, may be applied to the thermal image data (e.g., in the form of a separate vector for each pixel, in the form of a two-dimensional matrix in which one dimension represents successive pixels in a predetermined order and the other dimension represents successively acquired image data, or otherwise) to yield the equivalent wave representation (e.g., in the form of an equivalent wave vector or matrix).

The equivalent wave representation may be presented, e.g., on a display screen, as a series of images, where each image represents a depth within the object from the imaged surface. In each depth-resolved image, a discontinuity (e.g., corresponding to a flaw, inclusion, fracture, or other irregularity) in the material of the object at that imaged depth may be readily visible, e.g., as a bright or dark region within each displayed image. For example, each successive equivalent wave image frame (each at a later time) may represent increasing equivalent distance from the imaged surface, or equivalent depth, as determined by the wave velocity of the equivalent waves.

The equivalent depth of successive frames may increase until the equivalent depth is equal to the thickness of the object. When the equivalent depth is equal to the thickness of the object, the depth-resolved image may represent the rear surface of the object (e.g., the surface opposite the imaged surface). An image of the rear surface may include both images of discontinuities at the rear surface, as well as indications (e.g., shadows) of discontinuities that occurred at intermediate depths. Thus, an image of the rear surface may provide an overall view of the interior of the object (e.g., perhaps followed up by inspection of images of the depths at which a shadowed discontinuity actually was present).

In some cases, synthetic aperture processing may be applied to the data. For example, data in different pixels of the thermal image may be combined to create a synthetic aperture that resolves the direction from which the signal arrives; information that is not available in the original image. Application of synthetic aperture processing may increase spatial or contrast resolution of the images.

FIG. 1 schematically illustrates a system for equivalent wave field processing of thermal transient infrared images, in accordance with an embodiment of the present invention.

Thermal imaging system 10 is configured to acquire and process thermal images of an object 12. Thermal imaging device 18, e.g., in the form of a thermal camera or other device capable of acquiring a time sequence of thermal (e.g., infrared, terahertz, microwave, or other thermal radiation) images, is configured to acquire thermal images. In particular, thermal imaging device 18 may be configured (e.g., aimed at, focused on, or otherwise configured) to acquire thermal images of surface 14 of object 12. In some cases, surface 14 may include one or more sides of (e.g., at a corner or edge of) object 12 that may be imaged concurrently, may include a single side of object 12, may include a region of a flat or curved surface of object 12, or another part of object 12.

Surface 14 or another side or surface of object 12 may be irradiated with radiation from radiation source 16. For example, radiation source 16 may be configured to emit electromagnetic or other radiation that may be absorbed as heat by object 12. Radiation source 16 may be configured to irradiation an entire side of object 12 (flood illumination), or a limited region of object 12 (spot illumination).

Radiation source 16 may be configured to emit radiation in the form of one or more pulses (e.g., a period of higher intensity radiation preceded and followed by a period of lower intensity or no radiation), or to begin radiating at a predetermined time (radiation described as a step function). For example, radiation source 16 may include a flash source, such as a xenon flash lamp or other type of flash lamp, with short (e.g., a few millisecond) durations and negligible (e.g., compared to the time during which thermal measurements are made) rise and fall times. As another example, radiation source 16 may include an incandescent lamp source (e.g., switched on and off with a predetermined time sequence or pattern) where the duration of the pulse may be a few seconds and with appreciable rise and fall times.

Operation of radiation source 16, of thermal imaging device 18, or both, may be controlled by controller 20. In some cases, radiation source 16 and thermal imaging device 18 may be operated separately by an operator who starts and stops operation of each. In some cases, controller 20 may be configured to automatically coordinate operation of thermal imaging device 18 with operation of radiation source 16. For example, controller 20 may be configured to operate thermal imaging device 18 to begin acquiring images when a pulse of radiation is emitted by radiation source 16. Coordinated acquisition of images may begin concurrently with emission of the pulse, may begin a predetermined time prior to emission of the pulse, or a predetermined time after emission of the pulse. Acquisition of the images may continue for a predetermined duration, or may continue until an operator of thermal imaging system 10 stops acquisition of thermal images, emission by radiation source 16, or both.

Controller 20 may include a single device (e.g., housed within a single housing), or two or more local or remote separate devices. For example, controller 20 may include separate controllers for operation of radiation source 16 and thermal imaging device 18.

Controller 20 may include processor 22. Processor 22 may include one or more processing units, e.g. of one or more computers. Processor 22 may be incorporated into controller 20 (e.g., housed in a single housing with other components of controller 20), may be external to controller 20 and connected to controller 20 by a wired or wireless communication channel, or may function separately from other components of controller 20.

Processor 22 may communicate with data storage 24. Data storage 24 may include one or more fixed or removable, volatile or nonvolatile, local or remote memory or data storage units or devices. For example, data storage 24 may include a computer readable medium for storing program instructions for operation of processor 22. Data storage 24 may be utilized to store data or parameters for use by processor 22 during operation, or results of operation of processor 22.

For example, data storage 24 may be configured to store image data 28. Image data 28 may be stored in one or more formats that enable access and processing by processor 22. Image data 28 may include thermal image data that is acquired by thermal imaging device 18, thermal image data after initial processing (e.g., after one or more of calibration, normalization, artifact removal, or other initial processing), processed equivalent wave image data, or otherwise processed image data.

Data storage 24 may be configured to store transformation data 26 for use in transforming thermal image data to equivalent wave image data. For example, transformation data 26 may include data corresponding to one or more radiation sources 16, or one or more modes of using one or more radiation sources 16. Transformation data 26 may correspond to content of one or more transformation matrices W, one or more modified transformation matrices W', one or more inverse transformation matrices $W^{-1}$, or one or more inverse modified transformation matrices $W'^{-1}$. Transformation data 26 may include one or more excitation profiles $h(t_d)$, or other data or parameters that may be utilized in processing image data 28.

Processor 22 may be configured to operate in accordance with programmed instructions stored in data storage 24. Processor 22 may be configured to execute one or more software functions or modules. Such functions may include, for example, transformation 30 to apply transformation data 26 to image data 28 to transform thermal image data into equivalent wave data, and vice versa, in some cases. Transformation 30 may also include calculating transformation data 26 (e.g., on the basis of a type of radiation source 16 and type of virtual wave excitation) for immediate application to image data 28, or for storage on data storage 24 for later use. Principal component thermography 32 may be applied to identify a principal component of image data 28, e.g., in order to separate an imaged feature from noise. Synthetic aperture processing 34 may be applied to image data 28. Excitation profile processing 36 may extract an excitation profile from image data 28. Processor 22 may be configured to execute other functions.

Processor 22 may communicate with output device 28. For example, output device 28 may include a computer monitor or screen. Processor 22 may communicate with a screen of output device 28 to display acquired or processed image data 28, e.g., a series of equivalent wave images. Alternatively or in addition, output device 28 may include a printer, display panel, speaker, or another device capable of producing visible, audible, or tactile output.

Processor 22 may communicate with input device 26. For example, input device 26 may include one or more of a keyboard, keypad, pointing device, touchscreen, or other user operable input device or control for enabling a user to input data or instructions for operation of processor 22, or to control operation of one or more components of controller 20 or of thermal imaging system 10.

Figure 2:
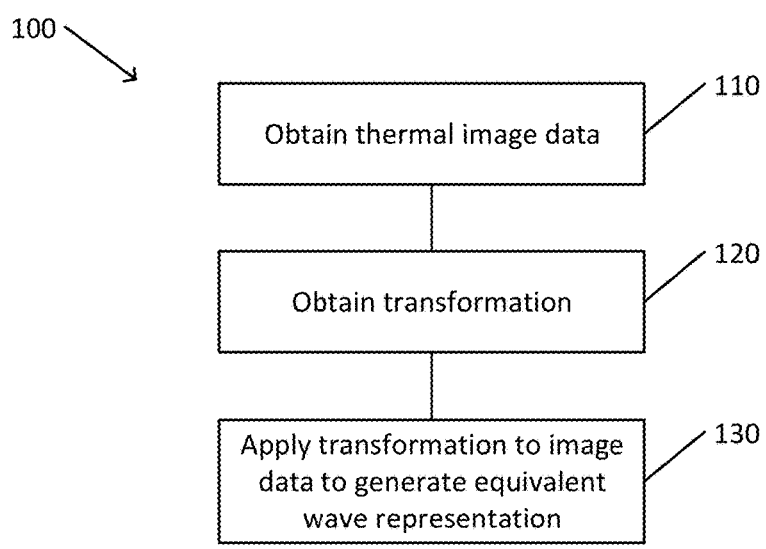
FIG. 2 is a flowchart depicting a method for equivalent wave field processing of thermal images, in accordance with an embodiment of the present invention.

FIG. 2 is a flowchart depicting a method for equivalent wave field processing of thermal images, in accordance with an embodiment of the present invention.

It should be understood, with respect to any flowchart referenced herein, that the division of the illustrated method into discrete operations represented by blocks of the flowchart has been selected for convenience and clarity only. Alternative division of the illustrated method into discrete operations is possible with equivalent results. Such alternative division of the illustrated method into discrete operations should be understood as representing other embodiments of the illustrated method.

Similarly, it should be understood that, unless indicated otherwise, the illustrated order of execution of the operations represented by blocks of any flowchart referenced herein has been selected for convenience and clarity only. Operations of the illustrated method may be executed in an alternative order, or concurrently, with equivalent results. Such reordering of operations of the illustrated method should be understood as representing other embodiments of the illustrated method.

Thermal imaging method 100 may be executed by processor 22 of controller 20. Thermal imaging method 100 may be executed automatically upon acquiring thermal image data from thermal imaging device 18, or may be executed upon receiving a command to do so, e.g., from an operator of thermal imaging system 10.

Thermal image data may be obtained (block 110).

For example, thermal image data may be acquired by operation of thermal imaging device 18 to acquire thermal images of surface 14 of object 12. The thermal image data may be acquired concurrently (e.g., simultaneously with or immediately following) irradiation of object 12 (e.g., on imaged surface 14, on a surface of object 12 that is opposite surface 14, or on another surface of object 12) by radiation source 16.

As another example, thermal image data that was previously acquired, as described above, may be retrieved, e.g., from image data 28 stored on data storage 24. The thermal image data typically represents a time series of thermal image frames taken of a surface 14 of an object 12 that is irradiated by one or more pulses emitted by radiation source 16.

A transformation to be applied to the thermal image data may be obtained (block 120).

For example, a previously calculated transformation (e.g., represented in the form of a matrix such as inverse transformation matrix $W^{-1}$, or otherwise) may be retrieved from a set of one or more stored transformations. The transformation may be retrieved based on the type of irradiation by radiation source 16 (e.g., spot or flood illumination, excitation profile), type of radiation source 16 (e.g., instantaneous flash, e.g., xenon or other flash, incandescent, or other radiation source), or other characteristics.

Alternatively, a transformation may be calculated. For example, a transformation in the form of inverse transformation matrix $W^{-1}$ may be calculated by inverting a transformation matrix W whose elements are calculated based on Laplace transforms of a virtual excitation (in the equivalent wave representation) and of a thermal excitation. The matrix inversion may be calculated using one or more techniques that are suitable for inverting an ill-posed matrix inversion (e.g., where the determinant of the matrix is very small). Such techniques include, for example, SVD and Tikhonov regularization.

In some cases, obtaining the transformation may include convolving the transformation matrix W with a previously obtained (e.g., based on measured results or modeled) excitation profile $h(t_d)$ to obtain a modified transformation matrix W'. The modified transformation matrix W' may be inverted to obtain an inverted modified transformation matrix $W'^{-1}$.

The obtained transformation may be applied to the obtained thermal image data (block 130).

For example, a pixel of a sequence of frames of the thermal image data may be arranged in the form of a set of vectors. Each vector of the set may represent a pixel of the sequence of thermal image frames, and each element of each vector may represent the value of a pixel at the time of acquisition of each frame. Each of the vectors may be multiplied by the transformation in the form of a two-dimensional matrix, such as inverse transformation matrix $W^{-1}$ or inverted modified transformation matrix $W'^{-1}$. One dimension of the matrix corresponds to the times of acquisitions of the frames of thermal image data (as in each of the vectors that represent the thermal image data), and the other dimension corresponds to times of virtual frames of the equivalent wave representation of the data. The transformation may be otherwise represented and applied.

The result of application of the transformation to all pixels of the sequence of thermal image frames may yield a set of virtual frames of an equivalent wave representation of the data. The sequence of virtual frames may represent successive surfaces at increasing depths within object 12 (e.g., the depth measured from imaged surface 14). Inhomogeneities in the structure of object 12 may appear as a region of increased reflection in the virtual frame that corresponds to the depth of the surface that includes an inhomogeneity. Similarly, inhomogeneities may appear as shadows in a virtual frame that corresponds to a depth that is deeper than the surface that includes the inhomogeneities. In some cases, examining a virtual frame that corresponds to a surface of object 12 that is opposite the imaged surface 14 (e.g., a deepest surface of object 12) may reveal all inhomogeneities in object 12, either as reflections or as shadows.

One or more of the virtual frames may be processed to enable display of a visual representation of the virtual frames.

In some cases, further processing may be applied to the equivalent wave representation.

Figure 3:
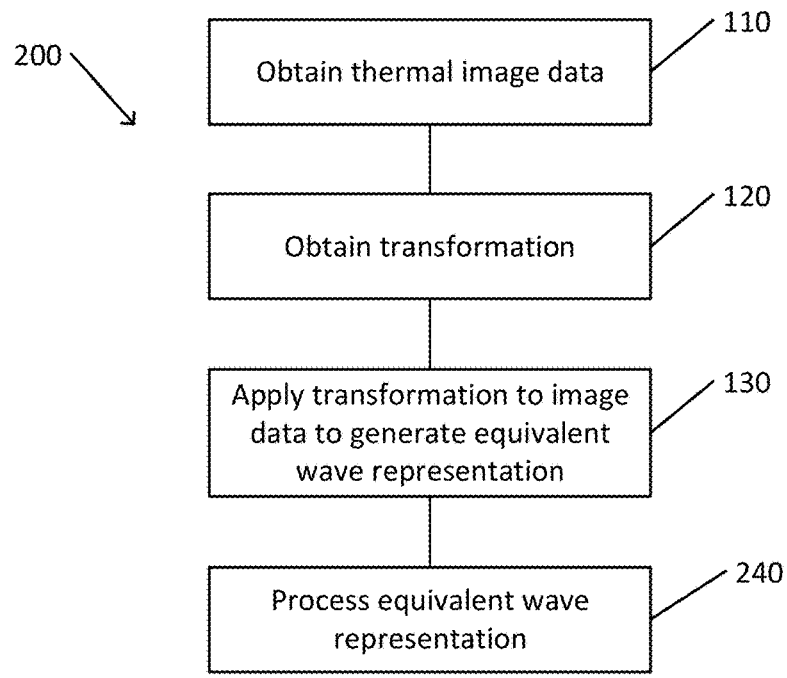
FIG. 3 is a flowchart depicting a variant of the method depicted in FIG. 2 that includes processing of the equivalent wave representation.

FIG. 3 is a flowchart depicting a variant of the method depicted in FIG. 2 that includes processing of the equivalent wave representation.

In thermal imaging method 200, after the transformation is applied to the thermal image data (block 130), further processing is applied to the equivalent wave representation (block 240).

For example, where appropriate (e.g., where thermal imaging device 18 is scanned relative to object 12), the processing may include application of synthetic aperture analysis. In synthetic aperture analysis, data in different pixels of the thermal image data may be combined to create a synthetic aperture that is larger than the actual aperture of thermal imaging device 18. Application of synthetic aperture analysis may enable increasing spatial or contrast resolution.

In some cases, processing may include application of principal component analysis. For example, principal component analysis may facilitate distinguishing of features of a virtual frame that represent structure of object 12 from noise or other artifacts. The principal component analysis may enable reducing the number of frames that are processed. In some cases, a transformation may be applied to the processed equivalent wave representation to transform back to processed thermal images.

In some cases, PCT may be applied to thermal image data to extract an excitation profile.

Figure 4:
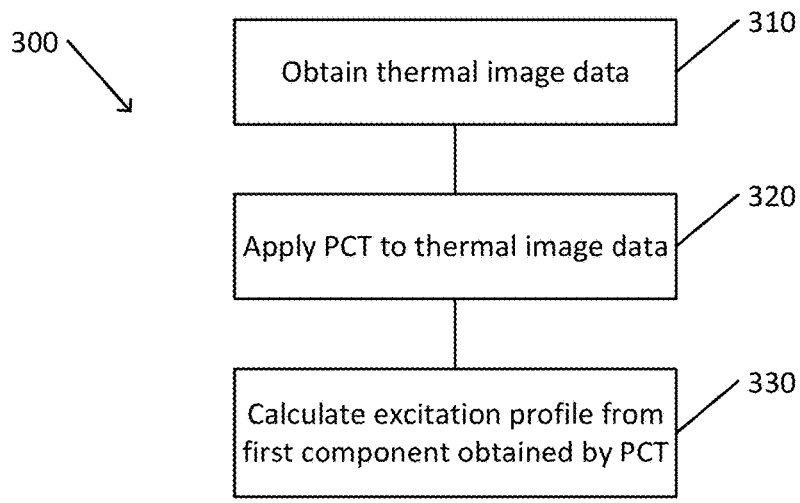
FIG. 4 is a flowchart depicting a method for extracting an excitation profile from thermal image data.

FIG. 4 is a flowchart depicting a method for extracting an excitation profile from thermal image data.

Thermal image data may be obtained, for example, by operating thermal imaging device 18 to acquire thermal images of surface 14 of object 12, or stored previously acquired thermal imaged data may be retrieved, e.g., from data storage 24 (block 310).

PCT may be applied to the thermal image data (block 320). For example, PCT analysis may yield a principal component that corresponds to the temperature response $T(t_d)$ of the surface of the object that is closest to a radiation source that is characterized by an excitation profile $h(t_d)$.

The excitation profile $h(t_d)$ may be calculated based on the temperature response $T(t_d)$ that results from the PCT analysis (block 330). Depending on the type of irradiation, excitation profile $h(t_d)$ may be derived from the temperature response $T(t_d)$. For example, in the case of flood illumination, excitation profile $h(t_d)$ may be calculated from the relationship $T(t_d)=a\ h(t_d)*t_d^{-1/2}$. In the case of spot illumination, excitation profile $h(t_d)$ may be calculated from the relationship $T(t_d)=a\ h(t_d)*t_d^{-3/2}$.

Different embodiments are disclosed herein. Features of certain embodiments may be combined with features of other embodiments; thus, certain embodiments may be combinations of features of multiple embodiments. The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

While certain features of the invention have been illustrated and described herein, many modifications, substitutions, changes, and equivalents will now occur to those of ordinary skill in the art. It is, therefore, to be understood that the appended claims are intended to cover all such modifications and changes as fall within the true spirit of the invention.

The invention claimed is:

1. A system for thermal transient imaging of an object, the system comprising:
    a radiation source configured to irradiate the object with radiation in accordance with an excitation profile;
    an imaging device comprising an array of detector pixels and configured to detect thermal radiation from a surface of the object;
    a processor configured to:
        obtain a series of frames of thermal image data of the surface acquired by the imaging device over time when the object is irradiated by the radiation source; and;
        process, using the excitation profile, the series of frames of thermal image data to transform the thermal image data to an equivalent wave field representation that represents a series of depth-resolved virtual images of the object, each depth-resolved virtual image representing a particular depth within the object from the surface; and
    a data storage that is configured to store one or a plurality of linear transformations that are applicable to the thermal image data to transform the thermal image data to the equivalent wave representation, each of the linear transformations that is applicable to a pixel of the time series of the frames that are acquired at times $t_d$ being representable by an inverse of a matrix of the form $$W(t_d, t_w) = \mathcal{L}^{-1}\left\{e^{-\sqrt{s}t_w}\frac{H_d(s)}{H_w(\sqrt{s})}, t_d\right\},$$

where $t_w$ represents a virtual time of each of the virtual images, $\mathcal{L}^{-1}$ represents the inverse Laplace transform, $H_d(s)$ represents a Laplace transform of thermal excitation by the radiation source, $H_w(\sqrt{s})$ represents the Laplace transform of a virtual wave excitation, and s is a Laplace transform variable.

2. The system of claim 1, wherein the virtual wave excitation is a Dirac delta function of $t_w$ or a derivative of the Dirac delta function of $t_w$.

3. The system of claim 2, wherein the virtual wave excitation is selected to be the Dirac delta function of $t_w$ when the radiation source is configured to irradiate the object with spot illumination, and to be the derivative of the Dirac delta function of $t_w$ when the radiation source is configured to irradiate the object with flood illumination.

4. The system of claim 1, wherein the thermal excitation is a Dirac delta function of $t_d$ or a step function of $t_d$.

5. The system of claim 1, wherein said transformation of said one or a plurality of transformations is representable as the inverse of the matrix W with an excitation profile of the radiation source.

6. The system of claim 5, wherein the processor is further configured to perform principal component analysis of the thermal image data to obtain the excitation profile.

7. The system of claim 6, wherein the processor is further configured to apply synthetic aperture processing to the thermal image data.

8. The system of claim 1, wherein the processor is further configured to apply principal component analysis to the equivalent wave field representation.

9. A method for thermal transient imaging of an object, the method comprising:
    obtaining a series of frames of thermal image data of a surface of the object that were acquired by an imaging device over time when the object is irradiated with radiation by a radiation source in accordance with a radiation profile;
    obtaining a transformation that corresponds to the radiation profile; and
    applying the transformation to the time series of frames to transform the thermal image data to an equivalent wave field representation that represents a series of depth-resolved virtual images of the object, each depth-resolved virtual image representing a particular depth within the object from the surface, wherein the transformation that is applicable to a pixel of the time series of the frames that are acquired at times $t_d$ comprises an inverse of a matrix of the form $$W(t_d, t_w) = \mathcal{L}^{-1}\left\{e^{-\sqrt{s}t_w}\frac{H_d(s)}{H_w(\sqrt{s})}, t_d\right\},$$

where $t_w$ represents a virtual time of each of the virtual images, $\mathcal{L}^{-1}$ represents the inverse Laplace transform, $H_d(s)$ represents a Laplace transform of thermal excitation by the radiation source, $H_w(\sqrt{s})$ represents the Laplace transform of a virtual wave excitation, and s is a Laplace transform variable.

10. The method of claim 9, wherein calculating the inverse comprises applying singular value decomposition or Tikhonov regularization to the matrix W.

11. The method of claim 9, wherein obtaining the transformation comprises selecting the virtual wave excitation to be a Dirac delta function of $t_w$ when the object is irradiated with spot illumination, and to be the derivative of the Dirac delta function of $t_w$ when the object is irradiated with flood illumination.

12. The method of claim 9, wherein the thermal excitation is a Dirac delta function of $t_d$ or a step function of $t_d$.

13. The method of claim 9, wherein obtaining the transformation further comprises convolving the matrix W with an excitation profile of the radiation source prior to inverting the matrix.

14. The method of claim 13, wherein obtaining the transformation further comprises performing principal component analysis of the thermal image data to obtain the excitation profile.

15. The method of claim 9, further comprising applying synthetic aperture processing to the thermal image data.

16. The method of claim 9, further comprising applying principal component analysis to the equivalent wave field representation.

* * * * *